(12) United States Patent
Brown et al.

(10) Patent No.: US 7,276,494 B2
(45) Date of Patent: Oct. 2, 2007

(54) PHOTOSENSITISERS

(75) Inventors: Stanley Beames Brown, Burley-in-Wharfedale (GB); Andrea Lucille Bell, Bradford (GB); John Griffiths, Leeds (GB); Jack Schofield, Mirfield (GB)

(73) Assignee: Photopharmica Limited, Leeds (GB)

( * ) Notice: Subject to any disclaimer, the term of this patent is extended or adjusted under 35 U.S.C. 154(b) by 376 days.

(21) Appl. No.: 10/393,783

(22) Filed: Mar. 21, 2003

(65) Prior Publication Data

US 2003/0180224 A1 Sep. 25, 2003

Related U.S. Application Data

(63) Continuation-in-part of application No. PCT/GB01/04224, filed on Sep. 21, 2001.

(30) Foreign Application Priority Data

Sep. 23, 2000 (GB) .................. 0023367.6

(51) Int. Cl.
- A61K 31/40 (2006.01)
- A61K 31/555 (2006.01)
- A61B 10/00 (2006.01)
- C07B 47/00 (2006.01)
- C07F 5/10 (2006.01)

(52) U.S. Cl. ............... 514/185; 514/410; 534/15; 540/145

(58) Field of Classification Search ........ 514/185, 514/410; 534/15; 540/145
See application file for complete search history.

(56) References Cited

U.S. PATENT DOCUMENTS 5,587,463 A 12/1996 Sessler et al.

FOREIGN PATENT DOCUMENTS

| EP | 0 322 795 | 9/1995 |
|---|---|---|
| EP | 0322795 B1 * | 9/1995 |
| JP | 64-68352 | 3/1989 |
| JP | 64-68696 | 3/1989 |
| JP | 64-70096 | 3/1989 |
| JP | 1-319702 | 12/1989 |
| JP | 4-322425 | 11/1992 |
| WO | WO98/30242 | 7/1998 |

OTHER PUBLICATIONS

Allen et al., "Photodynamic Therapy . . . ", Photochemistry and Photobiology (1999), 70(4), 512-23.*

(Continued)

*Primary Examiner*—James O. Wilson
*Assistant Examiner*—Paul V. Ward
(74) *Attorney, Agent, or Firm*—Morgan, Lewis & Bockius LLP

(57) ABSTRACT

A compound for use as a photosensitiser in PDT, in photochemical internalisation in the production of a cancer vaccine or in the diagnosis or detection of medical conditions, the compound having a photosensitising chromophoric system, a sulphonamido functionality and a carboxy functionality. The compounds used in the present invention are photosensitisers in PDT in vivo, and show phototoxic activity in vitro. The compounds are used to treat pre-cancerous conditions, cancer, ophthalmological disease, vascular problems, arteriosclerosis and restenosis and autoimmune diseases, skin diseases and other benign conditions, and for anti-microbial treatments.

12 Claims, 7 Drawing Sheets

OTHER PUBLICATIONS

Brasseur et al, "Receptor mediated targeting of phthalocyanines . . . ", Photochemistry and Photobiology (1999) 69(3), 345-52.*

Griffiths, et al., "Some observations on the synthesis of polysubstituted zinc phthalocyanine . . . ", Dyes and Pigments (1997), 33(1), 65-78.*

Mellish, K.J.; Vernon, D.I.; Schofield, J.; Griffiths, J.; Brown, S.B. Structure Activity Relationships of a Series of Tetra-Substituted Zinc Phthalocyanines Sep. 8, 1999. Centre for Photobiology and Photodynamic Therapy, University of Leeds, Leeds, United Kingdom.

"Photobleaching of Sensitisers Used in Photodynamic Therapy", Bonnet et al., Tetrahedron 57 (2001) 9513-9547.

"Tissue-Localazing Properties of Some Photosensitizers Studied by *in vivo* Fluroscence Imaging", Van Leengoed et al., Journal of Photoch. And Photobiol., B. biology 6 (1990), 111-119.

" Investigation of Cross-resistance to a Range of Photosensitizers, Hyperthermia and UV Light in Two Radiation-induced Fibrosarcoma Cell Strains Resistant to Photodynamic Therapy *In Vitro*", Oct. 17, 2000.

Mayhew et al., Photochemistry and Phtobiology, 2001, 73(1): 39-46.

"Effect of Light Fluence rate on Mammalian Celss Photosensitization by Chloroaluminium Phthalocyanine Tetrasulphonate", Ben-Hur et al., Inter. Journal of Radiation Biology, Sep. 26, 1986, vol. 51, No. 3, 467-476.

Patent Abstract of Japan vol. 014, No. 128 (Mar. 9, 1990) & JP 01-319702 (Dec. 26, 1989).

* cited by examiner

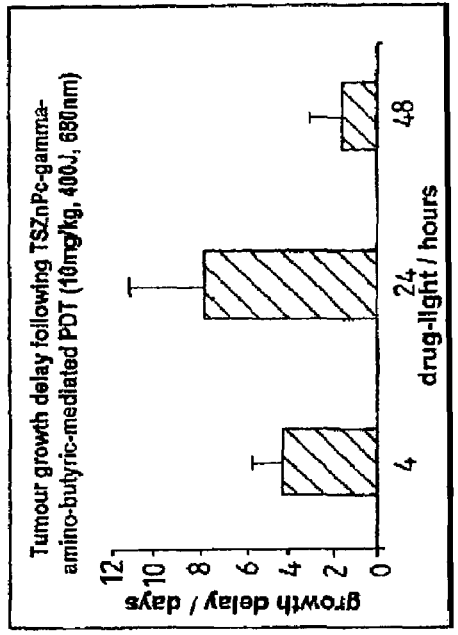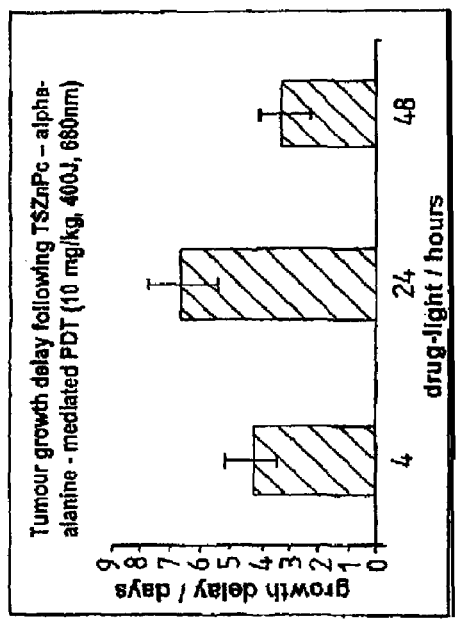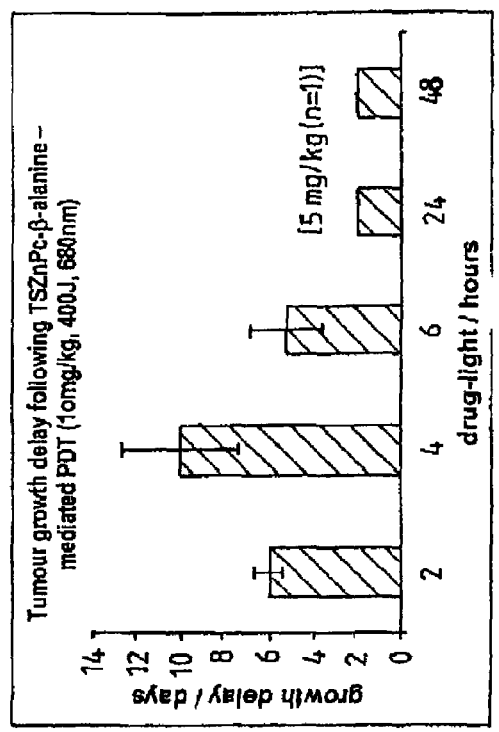

Area of necrosis following PDT with the β-alanine derivative at a 1h drug-light interval. Data points are the mean of at least 3 mice ± s.e.

Drugs were injected i.v, at 1.25 μmol/kg. Data points are the mean of at least 3 mice ± s.e.

Ear swelling response at 24h post-illumination. Bars represent the mean of 4 mice ± s.e.

Induced skin coloration following i.v. injection of sensitiser at 10mg/kg. Data series represents one rat.

PHOTOSENSITISERS

This application is a continuation-in-part of application no. PCT/GB01/04224 filed 21st Sep. 2001.

FIELD OF THE INVENTION

This invention relates to chemical compounds which act as photosensitisers and may be used in a type of medical treatment known as photodynamic therapy (PDT), as well as for the diagnosis and detection of medical conditions and related uses in photochemical internalisation, in the production of cancer vaccines and in the treatment of bacterial infections including photodisinfections.

BACKGROUND TO THE INVENTION

Photodynamic therapy is used in the treatment of cancer and other diseases. In this treatment a light absorbing compound (the photosensitiser) is applied to a tumour or other lesion. Subsequently laser light is used to activate the photosensitiser and the tumour tissue is destroyed in a process known as the photodynamic effect.

When the photosensitiser absorbs light it can produce a short-lived but highly active species known as singlet oxygen. Also produced by the activated photosensitiser is superoxide ion, $O_2^-$. Singlet oxygen is thought to be the main agent effective against the tumour although the superoxide ion may also participate.

It is believed that the photosensitiser destroys the blood supply to the malignant cells of the tumour, thereby ultimately starving the tumour of oxygen and nutrients. Alternatively, the photosensitiser may cause direct breakdown of tumour cells.

One photosensitiser currently used in PDT is a complex mixture of porphyrins (cyclic tetrapyrroles) known as haematoporphyrin derivative (HpD). A commercial version of HpD is available as Photofrin®. Although approved in various countries for treating various types of tumour, Photofrin has various limitations including the accumulation of the material in the skin for a prolonged period, thereby inducing undesirable photosensitivity under normal daylight.

Various other photosensitisers have been proposed for use in PDT. These include specific porphyrins, phthalocyanines, naphthalocyanines and chlorins. Sulphonated phthalocyanines have been reported to be particularly effective (Rosenthal, I., *Photochem. Photobiol.*, 1991, 53, 859-70).

Photosensitisers may also be used in the diagnosis and detection of medical conditions. For these applications, the photosensitiser is administered to the patient either internally or topically. Abnormal cells take up the photosensitiser to a greater extent than normal cells and, accordingly, when light is applied to the region under investigation an area containing abnormal cells will exhibit greater fluorescence than an area containing only normal cells.

Tetrasulphonylaminoglycine zinc (II) phthalocyanine (TGly) has been described in *J. Photochem. Photobiol B: Biology.*, 45 (1998) 28-35 as a potential agent for PDT. The performance of TGly as a photosensitiser in non-biological situations compared favourably with two clinically used photosensitisers and two others under test. However TGly was relatively poor in its ability to effect haemolysis of red blood cells and would therefore not be considered as a potential agent for use in PDT, diagnosis or detection applied to the human or animal body.

In general, there are various requirements, both chemical and biological, for a useful and clinically effective photosensitiser. The chemical properties include purity, a high quantum yield of singlet oxygen upon activation, the ability to be activated by wavelengths of light in the red to infra-red region (since such radiation penetrates deeply into tissue) and solubility in water. However, sensitisers which satisfy these chemical criteria do not necessarily possess advantageous biological properties for use in clinical PDT. These properties, which include localisation in target tissues (e.g. tumours), lack of skin photosensitivity, rapid clearance from the body and appropriate sub-cellular location are not predictable from chemical structure with current knowledge.

BRIEF DESCRIPTION OF THE DRAWINGS

The accompanying figures, which are incorporated in and constitute a part of this specification, illustrate several exemplary embodiments of the invention, but are not intended to limit the scope of the invention. Where present, and unless indicated otherwise, error bars indicate data representing the means of at least 3 rats±standard error.

FIG. 1(*b*) depicts tumour growth delay following TSZnPc-glycine-mediated photodynamic therapy at 680 nm (5/mg/kg, 400 J) measured at 4, 24 and 48 drug-light/hours.

FIG. 1(*c*) depicts tumour growth delay following TSZnPc-alpha-alanine-mediated photodynamic therapy at 680 nm (10/mg/kg, 400 J) measured at 4, 24 and 48 drug-light/hours.

FIG. 1(*d*) depicts tumour growth delay following TSZnPc-gamma-amino-butyric-mediated photodynamic therapy at 680 nm (10/mg/kg, 400 J) measured at 4, 24 and 48 drug-light/hours.

FIG. 1(*e*) depicts tumour growth delay following TSZnPc-beta-alanine-mediated photodynamic therapy at 680 nm (10/mg/kg, 400 J) measured at 2, 4, 6, 24 and 48 drug-light/hours.

STATEMENTS OF THE INVENTION

Figure 1A:
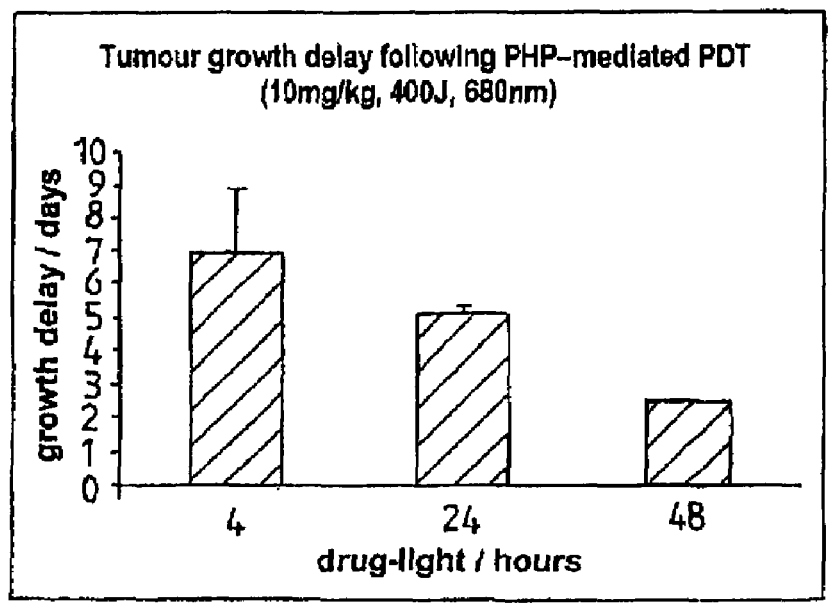
FIG. 1(*a*) depicts tumour growth delay following PHP-mediated photodynamic therapy at 680 nm (10/mg/kg, 400 J) measured at 4, 24 and 48 drug-light/hours.
Figure 1B:
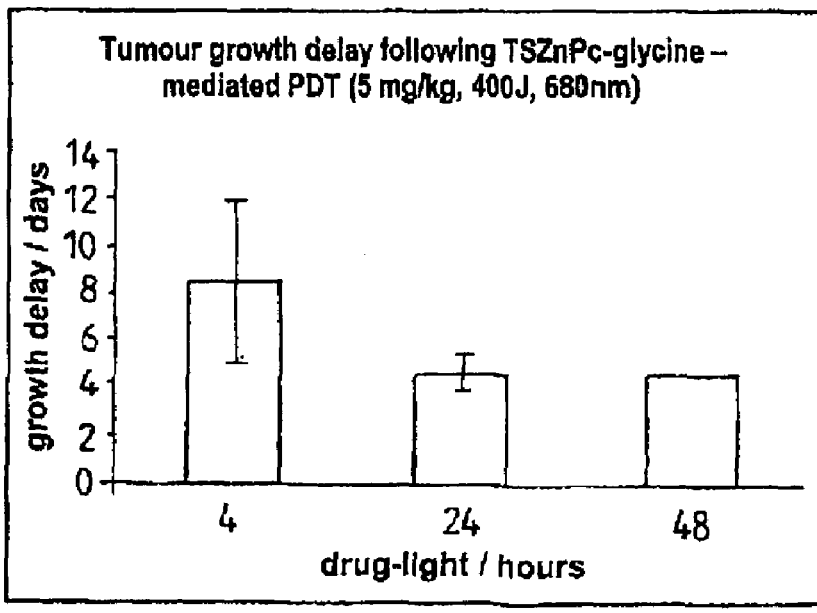

According to the present invention there is provided a compound for use as a photosensitiser in PDT, in photochemical internalisation in the production of a cancer vaccine or in the diagnosis or detection of medical conditions, the compound having a photosensitising chromophoric system, a sulphonamido functionality and a carboxy functionality.

The compounds used in the present invention are photosensitisers in PDT in vivo, and show phototoxic activity in vitro.

The photosensitising chromophoric system is preferably a residue of a metal-free phthalocyanine, a metal phthalocyanine, a benzoporphyrin, a purpurin, a chlorin, a bacteriochlorin, a tetraarylporphyrin, a porphycene or a texaphyrin, more preferably a residue of a metal phthalocyanine, a chlorin or a bacteriochlorin, especially a residue of a metal phthalocyanine. The sulphur of the sulphonamido functionality is preferably linked to the photosensitising chromophoric system. The sulphonamido and carboxy functionalities may be linked directly but are preferably linked by an optionally substituted, saturated or unsaturated, linear or branched hydrocarbon group which is represented by X and defined below.

According to a preferred feature of the present invention there is provided a compound for use as a photosensitiser in PDT, in photochemical internalisation in the production of a cancer vaccine or in the diagnosis or detection of medical conditions, the compound having the formula (I):

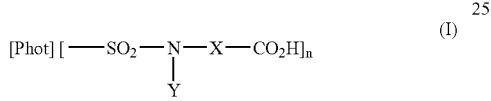
(I)

where:

Phot is a photosensitising chromophoric system, for example, a radical representing a photosensitising chromophoric system, such that the molecular species [Phot]Hn is capable of photosensitising Type I and Type II photoxidations;

X is optionally substituted linear or branched alkyl or alkenyl;

Y is hydrogen or optionally substituted linear or branched alkyl; and n is an integer of from 1 to 8, or a salt, preferably a pharmaceutically acceptable salt, thereof.

Phot may be [Phot$^1$] or [Phot$^1$Z] where each Phot and Phot$^1$ preferably is a residue of a metal-free phthalocyanine, a metal phthalocyanine, a benzoporphyrin, a purpurin, a chlorin, a bacteriochlorin, a tetraarylporphyrin, a porphycene or a texaphyrin, more preferably Phot is a residue of a metal-free phthalocyanine, a metal phthalocyanine, a chlorin or a bacteriochlorin, especially a residue of a metal-free phthalocyanine or a metal phthalocyanine, and most preferably a metal phthalocyanine. Z is as defined below.

In one preferred sub-group of compounds Phot is preferably a metal phthalocyanine, a benzoporphyrin, a purpurin, a chlorin or a bacteriochlorin.

The —CO$_2$H group in the compound of formula (I) may be in the form of a derivative such as an ester, amide, anhydride, but is preferably a —CO$_2$H group or a salt thereof. X is preferably linear or branched alkyl or alkenyl having from 0 to 5 carbon atoms, more preferably from 1 to 5 carbon atoms, and especially linear or branched alkyl or alkenyl having from 2 to 5 carbon atoms. The linear or branched alkyl or alkenyl represented by X is preferably unsubstituted or substituted by one or more hydrophilic groups, such hydrophilic groups are preferably selected from hydroxyl, methoxy, ethoxy, fluoro, chloro, carboxymethyl or carboxyamide. More preferably the linear or branched alkyl or alkenyl represented by X is unsubstituted.

Y is preferably H or linear or branched alkyl having from 1 to 5 carbon atoms, which optionally may be substituted preferably by one or more hydroxy groups, more preferably Y is H.

n is preferably an integer from 1 to 4, more preferably n is 1 or 4.

In one preferred sub-group of compounds of formula (I) X is preferably linear or branched alkyl having from 0 to 5 carbon atoms which optionally may be substituted by one or more hydrophilic groups, such as hydroxyl, methoxy, ethoxy or carboxy.

Preferred salts are those that retain sufficient solubility in water under ambient conditions to form stable compositions and medicaments and are non-toxic and salts of any substituted quaternary ammonium ion where the ion has no toxicity, especially preferred salts are those of lithium, potassium, sodium, calcium and magnesium.

The sulphonamido functionality, preferably via the S atom, is preferably linked directly to the photosensitising chromophoric system as shown for compounds of formula (I) or via the group —Z— in Phot$^1$Z. The compounds in which the sulphonamido functionality is linked to Phot$^1$Z are represented by formula (A):

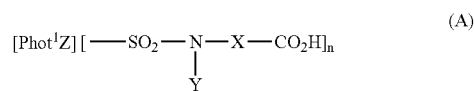
(A)

in which:

Z is a linking group; and

X, Y and n are as defined above.

The group Z is preferably a linear or branched alkyl, linear or branched oxyalkyl, linear or branched aminoalkyl or phenylene or —O-phenylene. Where Z is linear or branched alkyl, linear or branched oxyalkyl, linear or branched aminoalkyl the alkyl part is preferably C$_{1-6}$-alkyl, more preferably C$_{1-4}$-alkyl. Where Z is aminoalkyl the N atom of the aminoalkyl may carry a substituent R in which R is selected from H, CH$_3$—, C$_2$H$_5$—. Where Z is phenylene it is preferably 1,3-phenylene or 1,4-phenylene. Where Z is —O-phenylene it is preferably (1,3)—O—C$_6$H$_4$— or (1,4)—O—C$_6$H$_4$—

A further preferred sub-group of compounds in accordance with the present invention are phthalocyanine (Pc) derivatives which carry from 1 to 8 substituents of formula —SO$_2$NY—X—CO$_2$H or of formula —Z—SO$_2$NY—X—CO$_2$H in which X, Y and Z are as defined above. Preferred Pc derivatives are of formula (B):

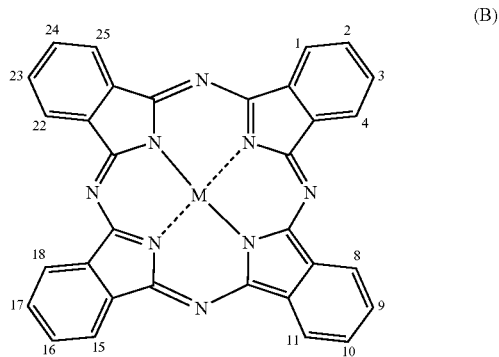
(B)

in which

M is a central atom or group.

M is preferably selected from H, Zn, ClAl, HOAl, Ca, Mg, Sn, ClGa, ClIn, HOIn, $Cl_2Si$, $(R^1O)_2Si$ in which $R^1$ is H or linear or branched $C_{1-10}$-alkyl, or $R^2O$—$(CH_2CH_2O)_p$ $CH_2CH_2$— in which $R^2$ is H, $CH_3$ or $C_2H_5$ and p is an integer from 1 to 4.

In the compound of formula (B) and formula (II) below the positions 2,3,9,10,16,17,23,24 are defined as "peripheral positions", the remaining 1,4,8,11,15,18,22,25 positions are defined as "non-peripheral positions" ["Phthalocyanine Materials" by N N McKeown, Cambridge, 1998, page 9].

The substituents of formula —$SO_2NY$—X—$CO_2H$ or —Z—$SO_2NY$—X—$CO_2H$ are preferably either attached to one or more peripheral positions or attached to one or more non-peripheral positions, more preferably they are attached to the peripheral positions. In compounds of formula (B) there are preferably from 1 to 4 substituents of formula —$SO_2NY$—X—$CO_2H$ or —Z—$SO_2NY$—X—$CO_2H$ attached to the peripheral positions, more preferably 1 or 4 substituents of formula —$SO_2NY$—X—$CO_2H$ or —Z—$SO_2NY$—X—$CO_2H$.

In compounds of formula (B), the substituents are preferably a —$SO_2NY$—X—$CO_2H$ group attached directly to the phthalocyanine benzene ring, or a —Z—$SO_2NY$—X—$CO_2H$ group in which Z is 1,3-phenylene, 1,4-phenylene, or any of the following in which the oxygen atom is attached to the phthalocyanine ring: (1,3)—O—$C_6H_4$—, (1,4)—O—$C_6H_4$—, —O—$(CH_2CH_2)_q$— where q is an integer from 2 to 4, X is preferably linear or branched $C_{2-5}$-alkyl and Y is preferably H.

The central atom, M, co-ordinates to two positions in the Pc ring system. Where M is monovalent, such as H, then two H atoms are present. Where M is divalent, such as Zn, then one Zn atom is present. Where M is trivalent, such as the Al in AlOH, the third valency is satisfied by the OH. Where M is tetravalent, such as the Si in $SiCl_2$, then the third and fourth valencies are satisfied by the two Cl's.

In compounds of formula (B) M is preferably Zn, ClAl, HOAl, $(R^1O)_2Si$ in which $R^1$ is H or linear or branched $C_{1-10}$-alkyl, more preferably Zn or HOAl and especially Zn. In a further preferred sub-group of compounds in accordance with the present invention are phthalocyanine (Pc) derivatives of formula (II):

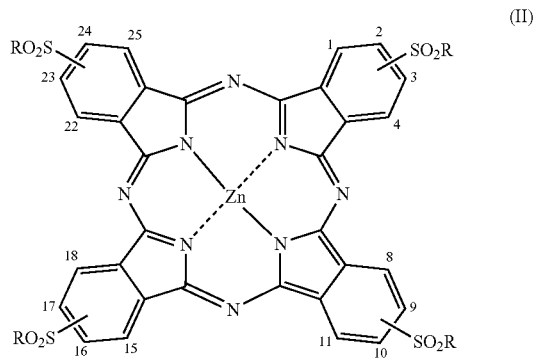

(II)

wherein:

each R independently is —NY—X—$CO_2H$, and X and Y are as defined above. In compounds of formula (II) Y is preferably H or linear or branched alkyl having from 1 to 5 carbon atoms, which optionally may be substituted preferably by one or more hydroxy groups, more preferably Y is H.

X is preferably selected from —$CH_2$— (referred to above as TGly and hereinbelow as TSZnPc-glycine), —$CH_2CH_2$— (TSZnPc-β-alanine), —$CH(CH_3)$— (TSZnPc-α-alanine), —$(CH_2)_3$— (TSZnPc-aminobutyric acid), —$(CH_2)_4$— (TSBuPc aminovaleric acid and —$(CH_2)_5$ (TSZnPc-aminocaproic acid).

In compounds of formula (II) the —$SO_2R$ substituent is preferably attached to one of the two peripheral positions in each ring, i.e. to one of positions 2 or 3, and 9 or 10, and 16 or 17, and 23 or 24.

A further preferred compound of the present invention is a compound of formula (II) except that only one of the rings carries an —$SO_2R$ substituent which is attached to one of positions 2 or 3 or 9 or 10 or 16 or 17 or 23 or 24.

Examples of other compounds falling within the scope of the present invention are as follows:

mono-, di-and tri-substituted analogues of the above shown tetra-substituted phthalocyanine structures, that is to say, compounds of the first-mentioned general formula (II) where n is 1, 2 or 3; chloroaluminium and hydroxyaluminium analogues of the mono-, di-, tri- and tetra-substituted zinc phthalocyanines; porphyrins bearing one or more of the sulphonyl amino acid side chains; benzoporphyrins bearing one or more of the sulphonyl amino acid side chains; chlorins bearing one or more of the sulphonyl amino acid side chains.

Where Phot is a chlorin it may be represented by formula (III):

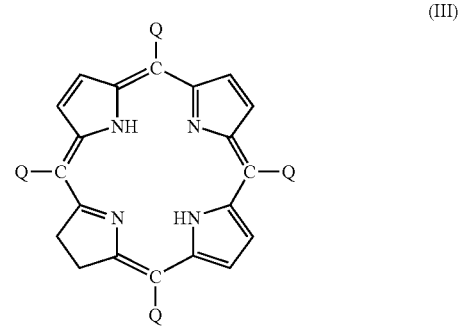

(III)

in which:

each Q independently is H or aryl optionally substituted by a group —$SO_2NY$—X—$CO_2H$ or —Z—$SO_2NY$—X—$CO_2H$ in which X, Y and Z are as defined above, provided that at least one Q is aryl substituted by a group —$SO_2NY$—X—$CO_2H$ or —Z—$SO_2NY$—X—$CO_2H$.

In compounds of formula (III) where Q is aryl it is preferably phenyl optionally substituted by a group —$SO_2NY$—X—$CO_2H$ or —Z—$SO_2NY$—X—$CO_2H$ in which X, Y and Z are as defined above.

The chlorin of formula (III) is a powerful singlet oxygen photosensitising chromophore, and has a useful absorption band in the red region of the spectrum, near 650 nm.

Where Phot is a benzoporphyrins may be represented by formula (IV):

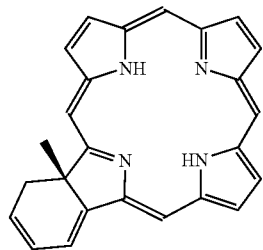

(IV)

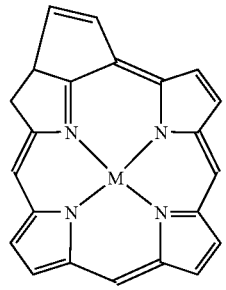

(VII)

As in the compounds of formula (III) the benzoporphyrins carry one or more Q groups bearing one or more sulphonyl amino acid side chains, and Q is as defined above.

Where Phot is a bacteriochlorin it may be represented by formula (V):

as in the compounds of formula (III) the purpurins carry one or more Q groups and Q and M are as defined above.

Where Phot is a tetraarylporphyrin it may be represented by formula (VIII):

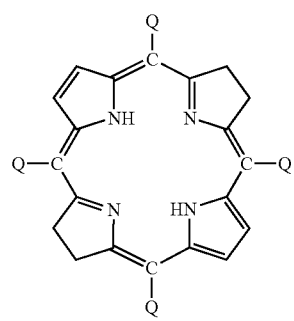

(V)

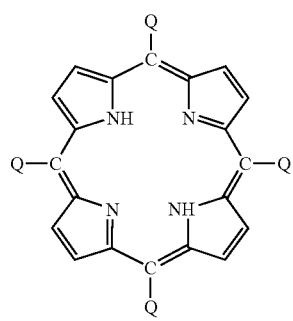

(VIII)

in which Q is defined as above.

Bacteriochlorins contain one formal double bond fewer than a corresponding chlorin, and the consequence is that they absorb at longer wavelengths than the latter, with an absorption peak above 730 nm.

Where Phot is a purpurin it may be represented by formulae (VI) and (VII):

as in the compounds of formula (III) the tetraarylporphyrins carry one or more Q groups and Q is as defined above.

Where Phot is a porphycene it may be represented by formula (IX):

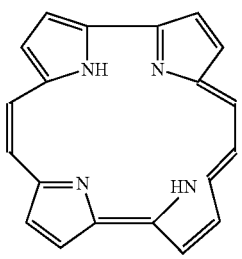

(IX)

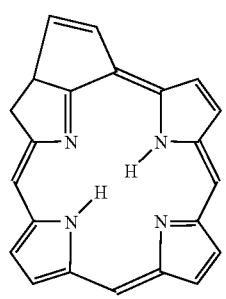

(VI)

as in the compounds of formula (III) the porphycenes carry one or more Q groups and Q is as defined above.

Where Phot is a texaphyrin it may be represented by formulae (X) and (XI):

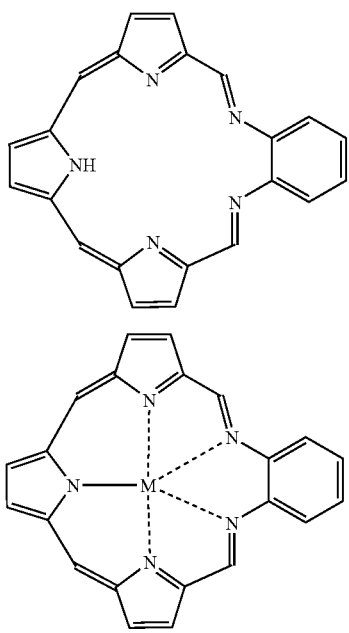

as in the compounds of formula (III) the texaphyrins carry one or more Q groups and Q and M are as defined above.

In the compounds of formula (III) to (IX) substituents may be attached to the pyrrole rings, such compounds and their uses form part of the present invention. Suitable substituents for the pyrrole rings may be selected from methyl, ethyl, propyl, isopropyl, carboxymethyl, carboxyethyl, methoxy and ethoxy.

Surprisingly, compounds of the invention not only are highly effective as photosensitising agents when used in vivo but also are rapidly cleared from the body, have little or no skin photosensitivity and unlike some other sensitisers, do not cause unacceptable skin discoloration.

According to a further feature of the present invention there is provided a use of a compound comprising a photosensitising chromophoric system, a sulphonamido functionality and a carboxy functionality as a photosensitising drug for PDT to treat pre-cancerous conditions (e.g. Barrett's oesophagus and cervical intraepithelial neoplasia), cancer (e.g. bladder cancer and colon cancer), ophthalmological disease including macular degeneration, vascular problems such as cardiovascular disease, arteriosclerosis and restenosis and autoimmune diseases such as rheumatoid arthritis, skin diseases such as psoriasis, acne and eczema and other benign conditions such as endometriosis and mennorrhagia. Compounds comprising a photosensitising chromophoric system comprising a sulphonamido functionality and a carboxy functionality are particularly effective and preferred for the treatment of pre-cancerous conditions (e.g. Barrett's oesophagus and cervical intraepithelial neoplasia), cancer (e.g. bladder cancer and colon cancer). Preferred compounds for use as photosensitising drugs for PDT are those of formulae (A), (B), and (I) to (XI).

Particularly preferred compounds for use as photosensitising drugs for PDT are those of formulae (B), and (II).

According to a further feature of the present invention there is provided a use of a compound comprising a photosensitising chromophoric system, a sulphonamido functionality and a carboxy functionality as photosensitising drugs for PDT for anti-microbial treatments for example for skin and wound infections, other local infections as well as in the treatment of dental bacterial disease. The anti-microbial treatments include those involving Gram negative bacteria and Gram positive bacteria, preferably they are used to treat Gram positive bacteria such as Streptococcus and Staphylococcus, including MRSA. Preferred compounds for use as photosensitising drugs for PDT for anti-microbial treatments are those of formulae (A), (B), and (I) to (XI).

According to a further feature of the present invention there is provided a use of a compound comprising a photosensitising chromophoric system, a sulphonamido functionality and a carboxy functionality as photosensitising drugs for PDT for use in photochemical internalisation and in the production of cancer vaccines through their photosensitising properties and in non-therapeutic uses such as in photodetection and photodiagnosis through their fluorescence properties. Preferred compounds as photosensitising drugs for PDT for use in photochemical internalisation and in the production of cancer vaccines are of formulae (A), (B), and (I) to (XI).

Photochemical internalisation (PCI) is a process by which photosensitisation may be used to assist with the uptake of drugs and other biologically active molecules into cells and into sub-cellular compartments within cells. Typically a photosensitising drug comprising one or more compounds of formulae (A), (B), and (I) to (XI) is administered to a living cell which may be in vitro or in vivo (for example in an animal or a human being). Within a short time interval, typically less than 4 hours, of the administration of the photosensitiser (either before or after), the drug or biologically active material is administered. The photosensitising drug may be administered systemically, for example through intravenous injection, or topically, for example through a spray or cream. Light from a suitable light source (i.e of a wavelength suitable for activating the photosensitising drug) is applied within a period of 6 hours following administration of the photosensitising drug. This causes a reversible change to sub-cellular structures in which the drug or biologically active material is located and frees up the drug or biologically active material enabling it to move to other sub-cellular locations which may be more effective for its biological activity. Further details of photochemical internalisation may be found in WO00/54802.

Compounds of the present invention may be useful in the treatment, diagnosis and/or detection of conditions in various parts of the body including the skin, lungs, brain, eye, colon, bladder, cervix and oesophagus.

It is found that the combination of the non-ionic polar sulphonamide residue and the weakly acidic carboxylic acid group results in the compound of the present invention having good water solubility allowing easy formulation of appropriate compositions for use in medical treatment.

The present invention also provides a pharmaceutical composition comprising one or more compounds comprising a photosensitising chromophoric system comprising a sulphonamido functionality and a carboxy functionality together with one or more pharmaceutically acceptable diluents, excipients or adjuvants. Suitable diluents include ethanol, polyethylene glycol, propylene glycol, DMSO, aqueous buffer solutions and physiological saline. Where the compound is very sparingly water-soluble agents may be used to aid solution such as Cremaphore®, an oil-based vehicle. Suitable excipients and adjuvants may generally be found in United States Pharmacopeia/National Formulary (2000); Remington's The Science and Practice of Pharmacy, Meade Publishing Co. Preferred pharmaceutical compositions comprises one or more compounds of formulae (A), (B), and (I) to (XI)

The present invention also provides compounds of formula (I), formula (II), formula (A) and formula (B), excluding the compounds tetrasulphonylaminoglycine zinc (II) phthalocyanine, tetrasulphonylamino β-alanine zinc (II) phthalocyanine, tetrasulphonylamino-α-alanine zinc (II) phthalocyanine, tetrasulphonylamino butyric acid zinc (II) phthalocyanine, tetrasulphonylamino valeric acid zinc (II) phthalocyanine, and tetrasulphonylamino caproic acid zinc (II) phthalocyanine. The excluded compounds may also be defined by reference to formula (II), the excluded compounds are those in which X is —$CH_2$— (referred to above as TGly and as TSZnPc-glycine), —$CH_2CH_2$— (TSZnPc-β-alanine), —$CH(CH_3)$— (TSZnPc-α-alanine), —$(CH_2)_3$— (TSZnPc-aminobutyric acid), —$(CH_2)_4$— (TSBuPc aminovaleric acid and —$(CH_2)_5$ (TSZnPc-aminocaproic acid).

The present invention also provides compounds of formulae (III) to (XI).

In addition the present invention provides the use of a compound comprising a photosensitising chromophoric system comprising a sulphonamido functionality and a carboxy functionality in the manufacture of a medicament for treatment of a condition by photodynamic therapy or for photochemical internalisation in the production of a cancer vaccine or in the manufacture of an agent for use as a photosensitiser in the diagnosis or detection of a medical condition. Preferred compound are those of formulae (A), (B), and (I) to (XI).

A further aspect of the present invention provides a method of treatment of the human or animal body which comprises administering to the body a compound comprising a photosensitising chromophoric system, a sulphonamido functionality and a carboxy functionality, and subjecting the body to PDT after administration of the compound.

Furthermore, the present invention provides a method of treatment of an animal, including a human being, by photodynamic therapy in which the photosensitiser comprises a compound of formulae (A), (B), and (I) to (XI) or a method of diagnosis or detection using a compound of formulae (A), (B), and (I) to (XI) as a photosensitiser.

The phthalocyanines of the present invention may be conveniently made by a number of methods, and details of these are provided in a review by N. B. McKeown entitled "Phthalocyanine Materials: Synthesis, Structure and Function", Cambridge University Press, 1998.

The porphyrins and chlorins of the present invention may be conveniently made by reacting four molecules of pyrrole with four molecules of the appropriate araldehyde under acid catalysed conditions, to give the tetra-aryl-substituted porphyrin. This can then be successively reduced and oxidised to give the chlorin as described in U.S. Pat. No. 4,992,257. Mono, di and tri-substituted porphyrins and then chlorins may be made by using appropriate ratios of substituted and unsubstituted pyrroles as starting materials. For example to obtain a predominantly mono-substituted porphyrins or chlorins 1 mole equivalent of the substituted pyrrole and 3 mole equivalents of unsubstituted pyrrole is used.

The benzoporphyrins of the present invention may be conveniently made in isomerically pure form from acetylvinylporphyrins by cycloaddition with suitable acetylenic compounds, this is described in 'New syntheses of benzoporphyrin derivatives and analogs for use in photodynamic therapy' by Meunier, Isabelle; Pandey, Ravindra K.; Walker, Michelle M.; Senge, Mathias O.; Dougherty, Thomas J.; Smith, Kevin M. Bioorganic & Medicinal Chemistry Letters (1992), vol. 2, pp 1575-80]. Again Mono, di and tri-substituted compounds may be made by selecting appropriate ratios of starting materials.

The bacteriochlorins of the present invention may be conveniently made as precursors to the chlorins by a method generally in WO00/73308.

The purpurins of the present invention may be conveniently made by methods described variously in; a)'Synthesis and structure of a 5,15-bis(4-pyridyl)purpurin' Forsyth, Timothy P.; Nurco, Daniel J.; Pandey, Ravindra K.; Smith, Kevin M. Tetrahedron Letters (1995), vol. 36, pp 9093-6; b) 'Use of the chlorophyll derivative, purpurin-18, for syntheses of sensitizers for use in photodynamic therapy' Lee, Shwn Ji H.; Jagerovic, Nadine; Smith, Kevin M. Dep. Chem., Univ. California, Davis, Calif., USA; c) Journal of the Chemical Society, Perkin Transactions 1: (1993), pp 2369-77. 'Production and use of purpurins, chlorins and purpurin- and chlorin-containing compositions' Morgan, Alan R.; Selman, Steven H.; Kreimer-Birnbaum, Martha; and in U.S. Pat. Nos. 5,051,415 and 5,216,012.

The tetraarylporphyrins of the present invention may be conveniently made by the method of Adler et al. [A D Adler F R Longo and J D Finarellis, J.Org.Chem,., 32, 476 (1967)].

The porphycenes of the present invention may be conveniently made by the general methods described in E Vogel, M Kocher, H Schmielder, J Lax 'Porphycene-a novel porphyrin isomer'. Agnew Chem 98, (1986) 262-263.

The texaphyrins of the present invention may be conveniently made by the general methods described in J L Sessler, G Hemmi, T D Mody et al, 'Texaphyrins: synthesis and applications'. Am Chem Soc Accounts Chem Res 27, (1994) 43-50; and in S Young, K Woodburn, M Wright et al 'Lutetium texaphyrin (PCI-0123): a near infrared watersluble photosensitiser'. Photochem. Photobiol. 63 (1996) 892-897.

DETAILED DESCRIPTION OF THE INVENTION

The invention will now be illustrated, by way of examples only, by reference to photosensitisers of formula II.

(A) Synthesis of Sensitisers (1) TSZnPc-β-alanine

Synthesis of Zinc Phthalocyanine Tetrasulphonyl Chloride

Method 1.

The sodium salt of zinc phthalocyanine tetrasulphonic acid (5.0 g) was added with stirring to chlorosulphonic acid (58 ml) at ambient temperature, then heated to 55° C. for 2 hours. Thionyl chloride (7.5 ml) was then added slowly and stirring continued for a further 4 hours at 50-55° C. The mixture was allowed to cool and stirred overnight at room temperature, and ice was then added with vigorous stirring, giving a final volume of 500 ml. The blue solid was filtered off, washed well with ice-water, and dried as much as possible on the vacuum pump. The filter cake was then used immediately for subsequent reactions with amines.

Method 2.

To a stirred mixture of zinc phthalocyanine tetrasulphonic acid (4 g), dimethylacetamide (10 ml), and acetonitrile (40 ml) was added phosphorus oxychloride (15 ml) dropwise over 15 minutes. The mixture was then warmed to 60° C., held at that temperature for 1 hour, cooled to room temperature, and then ice/water was added with vigorous stirring. The precipitated tetrasulphonyl chloride was filtered off, washed well with ice/water, dried as much as possible at the filter pump, and the filter cake was used immediately for the preparation of derivatives.

Conversion to TsZnPc-β-alanine.

The tetrasulphonyl chloride filter cake made from 5.0 grams of zinc phthalocyanine tetrasulphonic acid was added to a solution of β-alanine (12 g) in a mixture of dimethylformamide (45 ml) and dimethylacetamide (5 ml), simultaneously adding dropwise dilute sodium hydroxide solution to ensure slight alkalinity. The solution was then stirred for 12 hours at ambient temperature, diluted with water (100 ml), and dialysed for 1 week with frequent changes of water. The dialysed solution was then evaporated to dryness and dried in the oven to give TsZnPc-β-alanine (1.4 g).

Found: C, 35.3; H, 3.3; N, 10.8%.

$C_{44}H_{32}N_{12}O_{16}S_4ZnNa_4$. $12H_2O$ requires: C, 35.5; H, 3.8; N, 11.3%.

Molar absorption coefficient=124,260 1 $mol^{-1}$ $cm^{-1}$ in DMF at $\lambda_{max}$ 672 nm (2) TsZnPc-α-alanine The procedure described in Example 1 was followed, using 5 grams of zinc phthalocyanine tetrasulphonyl chloride and 12 grams of α-alanine. The resultant solution was dialysed for 1 week with frequent changes of water, and then evaporated to dryness and the residue dried in an oven to give TsZnPc-α-alanine (1.27 g).

Found: C, 36.45; H, 3.55; N, 11.7%.

$C_{44}H_{32}N_{12}O_{16}S_4ZnNa_4$. $10H_2O$ requires C, 36.44; H, 3.59; N, 11.6%.

Mass spectrum (electrospray): Found M 1180; $C_{44}H_{36}N_{12}O_{16}S_4Zn$ requires M=1180.

Molar absorption coefficient=141,400 1 $mol^{-1}$ $cm^{-1}$ in DMF at $\lambda_{max}$=672 nm (3) TsZnPc-aminobutyric Acid Zinc phthalocyanine tetrasulphonic acid (4.0 g) was converted into the tetrasulphonyl chloride and the filter cake was added to a solution of 4-aminobutyric acid (6.5 gm) in dimethylformamide (45 ml) and dimethyl acetamide (5 ml), simultaneously adding dropwise dilute sodium hydroxide solution to maintain slight alkalinity. The solution was stirred for 12 hours at ambient temperature, diluted with water (50 ml) and dialysed for 1 week with frequent changes of water. The dialysed solution was then evaporated to dryness and the residue dried in an oven to give TsZnPc-aminobutyric acid (1.11 g).

Found: C, 39.4; H, 3.5; N, 12.5%.

$C_{48}H_{40}N_{12}O_{16}S_4Zn$ $Na_4$. $6H_2O$ requires: C, 40.2; H, 3.6; N, 11.7%.

Molar absorption coefficient=103,000 1 $mol^{-1}$ $cm^{-1}$ in DMF at $\lambda_{max}$=672 nm (4) TsZnPc-aminovaleric acid Zinc phthalocyanine tetrasulphonic Acid (5.0 g) was converted into the tetrasulphonyl chloride and the filter cake was added to a solution of 5-aminovaleric acid (5 g) in dimethylformamide (45 ml) and dimethylacetamide (5 ml), simultaneously adding dropwise dilute sodium hydroxide to maintain slight alkalinity. The solution was stirred for 12 hours at ambient temperature, diluted with water (50 ml) and dialysed for 48 hours with frequent changes of water. The dialysed solution was evaporated to dryness and the blue residue dried in an oven to give TsZnPc-aminovaleric acid (1.40 g).

Found C=40.0; H, 3.8; N, 11.75%, $C_{52}H_{48}N_{12}O_{16}S_4Zn$ $Na_4$. $10H_2O$ requires C, 40.0; H, 4.4; N, 10.8%

Molar absorption coefficient=72,000 1 $mol^{-1}$ $cm^{-1}$ in DMF at $\lambda_{max}$ 672 nm (5) TsZnPc-aminocaproic acid Zinc phthalocyanine tetrasulphonic acid (5.0 g) was converted into the tetrasulphonyl chloride and the filter cake was added to a solution of 6-aminocaproic acid (7.0 g) in dimethylformamide (45 ml) and dimethylacetamide (5 ml), simultaneously adding dilute sodium hydroxide solution to maintain slight alkalinity. The solution was stirred for 12 hours at ambient temperature, diluted with water (50 ml), and dialysed for 48 hours with frequent changes of water. The dialysed solution was evaporated to dryness and the residue dried in the oven to give TsZnPc-aminocaproic acid (1.16 g).

Found C=39.7%; H=3.8%; N=11.1%, $C_{56}H_{56}N_{12}O_{16}S_4Zn$ $Na_4$. $10H_2O$ requires C=41.5%; H=4.7%; N=10.4%

Molar absorption coefficient=106,000 1 $mol^{-1}$ $cm^{-1}$ in DMF at $\lambda_{max}$ 672 nm.

(6) Synthesis of zinc phthalocyanine-2-(N-2-carboxyethyl)sulphonamide (a) Zinc phthalocyanine-2-sulphonic acid [ref.: "Syntheses and analyses of sulfonated phthalocyanines". H. Ali, R. Langlois, J. R. Wagner, N. Brasseur, B. Paquette, and J. E. Van Lier, Photochemistry and Photobiology (1988), vol 47, pp 713-17] was first converted to its acid chloride by reaction with phosporous oxychloride. Thus the sulphonic acid (1.0 g) was stirred in a mixture of acetonitrile (10 ml) and dimethylacetamide (2 ml), and to this at room temperature was added phosphorous oxychloride (2.0 ml) dropwise. The temperature rose to 35° C. and the mixture was then heated at 50-55° C. for 1.5 h. The mixture was stirred at room temperature for a further 12 hours. Ice-water (100 ml) was added and the blue precipitate was filtered off, washed with ice water until the washings were no longer acid, and then washed with a little diethyl ether and pulled as dry as possible at the vacuum pump. The product was used immediately for the next step:

(b) Beta-alanine (2.5 g) and diazabicycloundecene (2.5 g) were added to a mixture of acetonitrile (25 ml) and dimethylacetamide (2.5 ml) and stirred at room temperature until dissolved. To this was added the sulphonyl chloride prepared in the previous step and the mixture was stirred at 25° C. for 12 hours. Water (50 ml) was added and the deep blue solution was transferred to dialysis tubing and dialysed in distilled water for 1 week, with frequent changes of the external distilled water. The contents of the tubing were then evaporated to dryness under vacuum, and the blue residue was heated in acetone, the suspension cooled and filtered to give zinc phthalocyanine-2-(N-2-carboxyethyl)sulphonamide as a dark blue solid.

[Microanalysis: Found: C, 46.3; H, 4.5; N, 13.9%. C35H21N9SO4.10H2O requires C, 46.1; H, 4.7; N, 13.8%.

C:N ratio, found 3.3, expected 3.3.]

In vitro photodynamic activity for zinc phthalocyanine-2-(N-2-carboxyethyl)sulphonamide compared with Zinc phthalocyanine tetrasulphonic acid. The sensitiser was tested by incubation with RIF-1 tumour cells at various dose rates, and measuring the cell kill by MTT assay after exposure to 665 nm laser radiation for a fixed time. The results were compared with zinc phthalocyanine tetrasulphonic acid as a control, and were expressed as the LD50 value for the sensitisers. Average LD50 results were:

Zinc Phthalocyanine Tetrasulphonic Acid:

Dark: no cell kill detectable
Light: LD50>10 micromolar

Zinc phthalocyanine-2-(N-2'-carboxyethylsulphonamide):
Dark: no cell kill detectable
Light: LD50 0.2 micromolar Thus in vitro, the mono-beta-alanine derivative is at least 50 times more PDT active than the tetrasulphonic acid.

(7) Synthesis of chlorin meso-tetrakis(4-sulphonyl amino acid) Derivatives (IIIa)

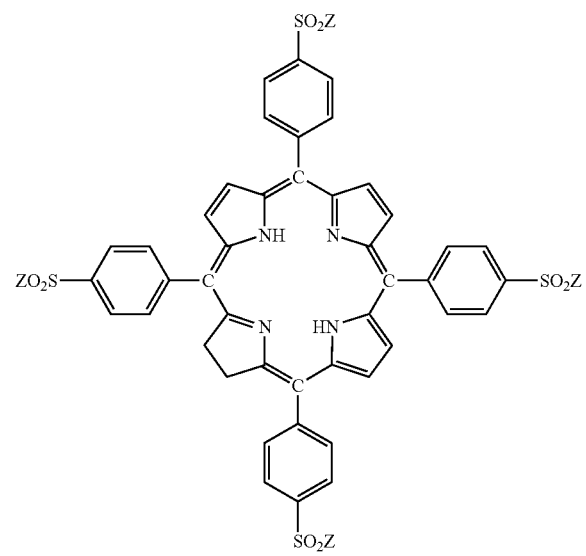

(IIIa)

(a) Synthesis of 5,10,15,20-tetrakis(4-sulfonatophenyl) chlorin (IIIa, Z=OH)

This is described by TPG Sutter and P Hanbright, in Inorganic Chemistry (1992), vol. 31, pp 5089-1093.

(b) Conversion to the Tetrasulphonyl Chloride (IIIa, Z=Cl)

A convenient and mild method would be that described for zinc phthalocyanine-2-sulphonyl chloride earlier, using phosphorous oxychloride in a mixture of acetonitrile and dimethylacetamide, with diazabicylcoundecene as base.

(c) Conversion of the Tetrasulphonyl chloride to the Tetra-Sulphonyl Amino acid derivative (IIIa, Z=—NH(CH$_2$)$_q$ CO$_2$H, q=1-5).

A similar procedure to that described for zinc phthalocyanine-2-(N-2-carboxyethyl)sulphonamide previously can be used. Thus the appropriate amino acid (20 mmol) and diazabicycloundecene (10 mmol ) in a mixture of acetonitrile (25 ml) and dimethylacetamide (2.5 ml) are stirred at room temperature until dissolved. To the solution is added the tetrasulphonyl chloride (2 mmol).and the mixture stirred at 25° C. until judged complete by thin layer chromatography. Water (50 ml) is added and the solution transferred to dialysis tubing and dialysed in distilled water for 1 week, with frequent changes of the external distilled water. The contents of the tubing are then evaporated to dryness under vacuum, and the residue heated in acetone, cooled and filtered off, to give (IIIa; Z=—NH(CH$_2$)$_q$CO$_2$H, q=1-5).

(B) Phototoxicity of Various Compounds Towards Cells in Culture

The following table (Table 1) shows the photocytotoxic activity of various compounds in accordance with the present invention in killing RIF-1 (murine fibrosarcoma) cells in culture.

TABLE 1

| Photosensitiser | X | 2h LD$_{50}$ (μM) (mean ± SD, n 3) |
|---|---|---|
| TSZnPc-glycine | —CH$_2$— | 142 ± 37 |
| TSZnPc-β-alanine | —(CH$_2$)$_2$— | 109 ± 31 |
| TSZnPc-α-alanine | —CH(CH$_3$)— | 109 ± 39 |
| TSZnPc-aminobutyric acid | —(CH$_2$)$_3$— | 90 ± 30 |
| TSZnPc-aminovaleric acid | —(CH$_2$)$_4$— | 125 ± 13 |
| TSZnPc-aminocaproic acid | —(CH$_2$)$_5$— | 104 ± 14 |

[Phot]=Zinc Phthalocyanine; n=4; LD$_{50}$ is the concentration of drug needed to cause 50% cell death in two hours of illumination (C) Photoactivity of Various Compounds Towards Tumours Data are shown in two animals models, the rat and the mouse. Comparative data are also shown for PHP (analogous to Photofrin). Growth delay measures the additional time taken for a treated tumour to grow to a given size, compared with an untreated tumour. Zero growth delay signifies no effect and growth delays of 5 days or longer imply substantial PDT activity. In both models, it is clearly seen that certain compounds of the present invention have at least equal and in some cases considerably higher photoactivity than PHP (Photofrin).

(1) PDT-Induced LSBD$_1$ Tumour Growth Delay in BDIX Rats

Sub-cutaneous tumours were treated interstitially with light from Cu-vapour laser (400 J, 100 mW at 680 nm for phthalocyanines and 630 nm for PHP (alternative name for commercial drug Photofrin).

Tumour growth delay is calculated as the number of days for treated tumour to reach a mean diameter of 15 mm minus the number of days for a control tumour to reach a mean diameter of 15 mm. Data for various compounds are shown in Table 2, which also indicates the times (drug-light interval) at which effects occurred.

Figure 2:
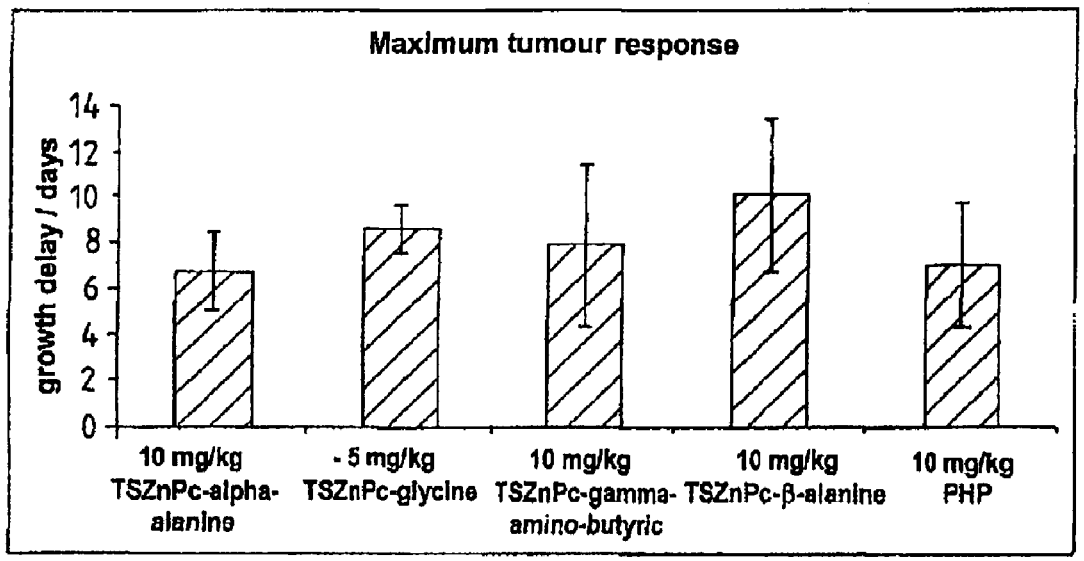
FIG. 2 depicts the maximum tumour growth delay obtained for the identified test compounds.

FIGS. 1a) and 1e) show tumour growth delay at different drug-light intervals for the compounds tested. Where error bars are shown data given are the means of at least 3 rats±s.e. FIG. 2 shows the best response obtained for each compound tested.

Figure 3:
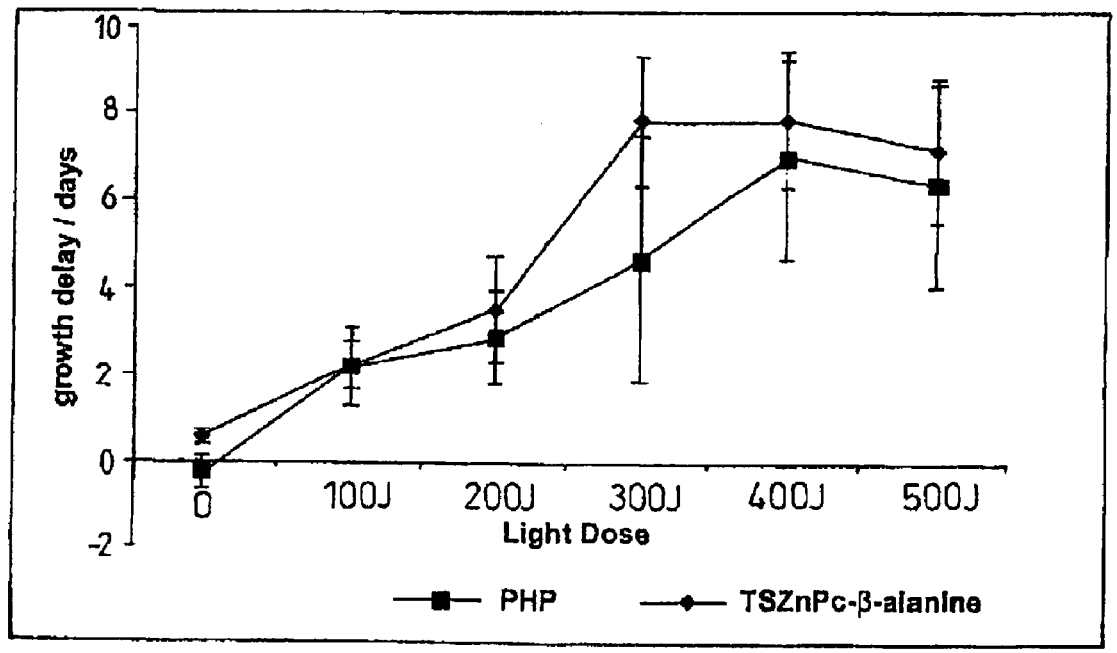
FIG. 3 depicts light dose-response curves for PHP (alternative name for the commercial drug Photofrin) and TSZnPc-beta-alanine. Data points are the mean of 6 rats±standard error.

FIG. 3 shows light dose response curves for PHP and the β-alanine pc derivative. Data points are the mean of 6 rats±s.e.

TABLE 2

| Drug | Drug dose (mg/kg) | Drug-light interval (h) | | | | |
|---|---|---|---|---|---|---|
| | | 2 | 4 | 6 | 24 | 48 |
| TSZnPc-β-alanine | 10 | 6 ± 0.62 | 10 ± 2.62 | 5.25 ± 1.59 | 2 (5 mg/kg) | 2 (5 mg/kg) |
| TSZnPc-Glycine | 5 | | 8.5 ± 3.5 | | 4.7 ± 0.75 | 4.5 |
| TSZnPc-α-alanine | 10 | | 4.33 ± 0.83 | | 6.67 ± 1.09 | 3.33 ± 0.73 |
| TSZnPc-γ-amino-butyric | 10 | | 4.3 ± 1.44 | | 7.83 ± 3.33 | 1.67 ± 1.53 |
| PHP | 10 | | 7 ± 1.87 | | 5.17 ± 0.17 | 2.5 |

(2) PDT-Induced Area of Necrosis in CaNT Tumours (in CBA/Gy Mice)

Figure 4:
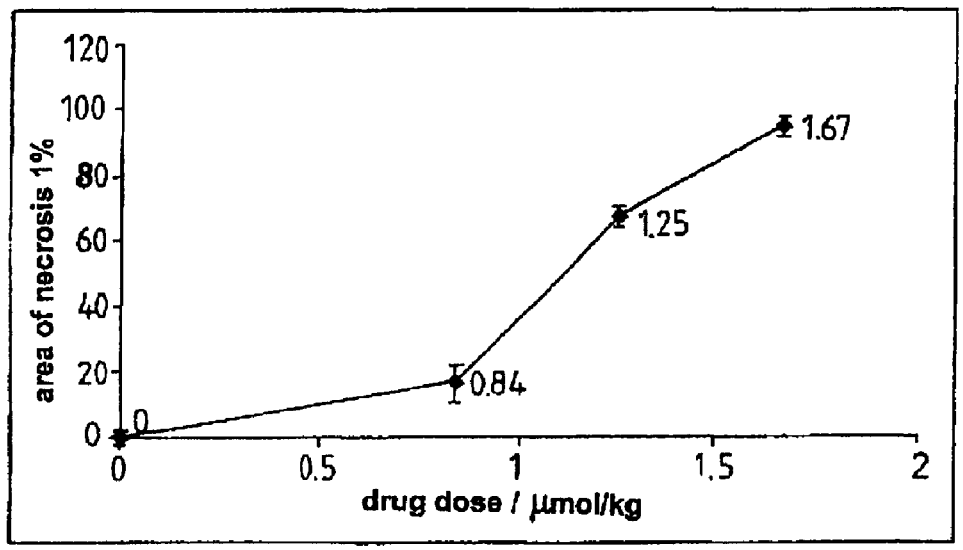
FIG. 4 depicts a dose-response curve measuring the area of necrosis for the TSZnPc-beta-alanine derivative.
Figure 5:
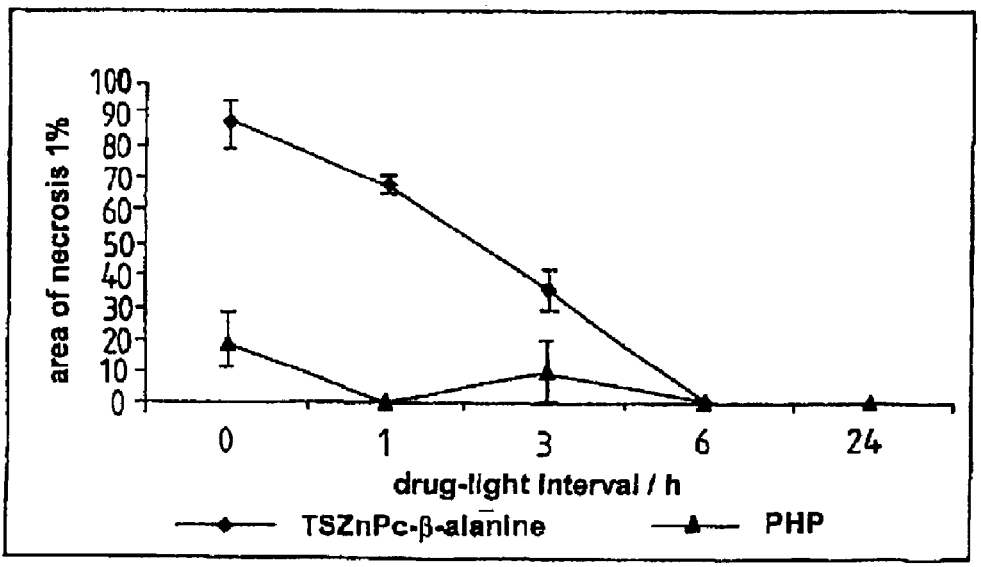
FIG. 5 depicts the comparison between PHP and TSZnPc-beta-alanine at equimolar amounts, measuring the area of necrosis at different drug light/hours.

Sub-cutaneous tumours were treated superficially with light from the Paterson xenon arc lamp (60J/cm$^2$, 50 mW/cm$^2$). For PHP a 630±15 nm filter was used, for the β-alanine derivative 685±15 nm filter was used. At 72 h post PDT mice were killed and area of necrosis was determined from a mid-section of tumour FIG. 4 shows a dose-response curve for the β-alanine derivative. FIG. 5 compares PHP and the β-alanine derivative at equimolar amounts at different drug-light intervals.

(D) Skit Photosensitivity Measurements

Skin photosensitivity is a major problem with some currently-used photosensitisers.

Patients sometimes have to avoid light after drug administration for several weeks.

The following data show skin photosensitivity scores for various compounds of the present invention, compared with PHP (Photofrin) in both rat and mouse models. There are clear advantages of some compounds of the present invention in having very low or zero skin photosensitivity.

(1) Skin Photosensitivity-Visual Assessment in Rodent Skin Patch

Figure 6:
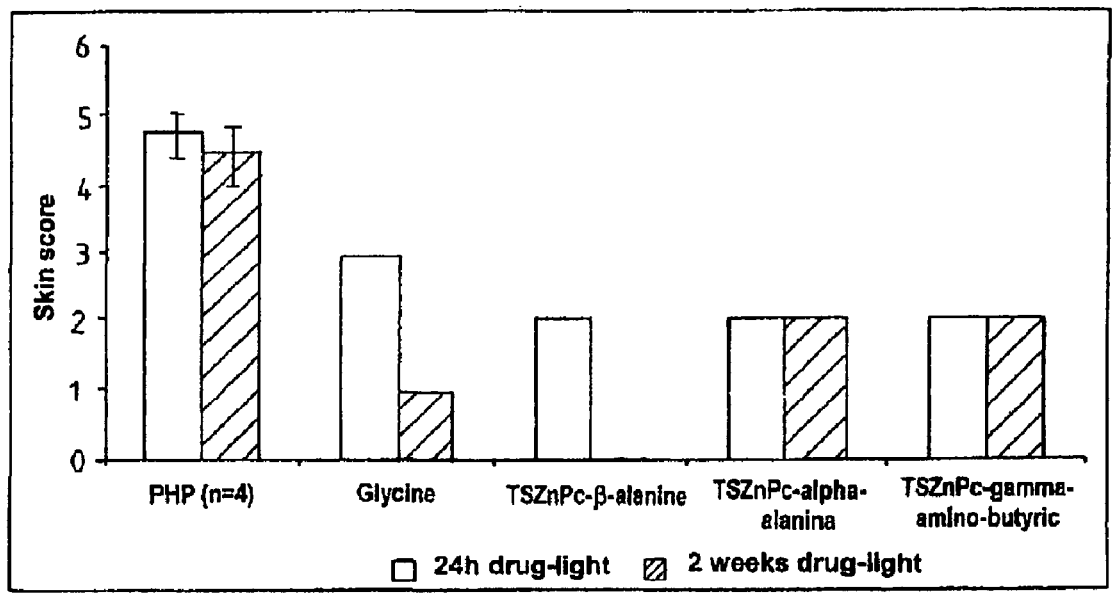
FIG. 6 depicts the skin reaction experienced by wistar rats at 24-hour and 2-week post-illumination using the identified test compounds.

The skin of wistar rats was depilated and rats were injected with sensitiser (i.v.) at 0.5, 2, 5 or 10 mg/kg. At 24 h the skin patch was exposed to broad band white light from a xenon arc lamp (91.8 J cm$^{-2}$). Light exposure was repeated on untreated skin at 2 weeks post-drug injection. Skin reactions were scored according to Table 3. Data are shown in Table 4 and in FIG. 6.

TABLE 3

| Skin Reaction | Score |
|---|---|
| No visible change | 0 |
| Doubtful changes, possibly some transient erythema or oedema. | 1 |
| Definite oedema or erythema healing within a few days | 2 |
| Severe ordenta or erythema leading to dry desquamation, scaling or crusting. | 3 |
| Indurations with some reddening or dry desquamation to treatment area, (oedema of surrounding arm). | 4 |
| Indurations with reddening leading to escar formation of part of treatment area (ocdema of surrounding area). | 5 |
| Indurations and reddening teading to esear formation of whole of treatment area (oedema of surrounding area) | 6 |
| No defined treatment areas, oedema and extensive necrosis also affecting untreated area. | 7 |

TABLE 4

| | Skin score (at 10 mg/kg) | |
|---|---|---|
| Drug | 24 h drug-light | 2 wks drug-light |
| PHP (n = 4) | 4.75 ± 0.34 | 4.5 ± 0.35 |
| TSZnPc-Glycine (n = 1) | 3 | 1 |
| TSZnPc-β-alanine Pc (n = 1) | 2 | 0 |
| TSZnPc-α-alanine Pc (n = 1) | 2 | 2 |
| TSZnPc-γ-amino-butyric Pc (n = 1) | 2 | 2 |

(2) Skin Photosensitivity Murine Ear Swelling Response

Figure 7:
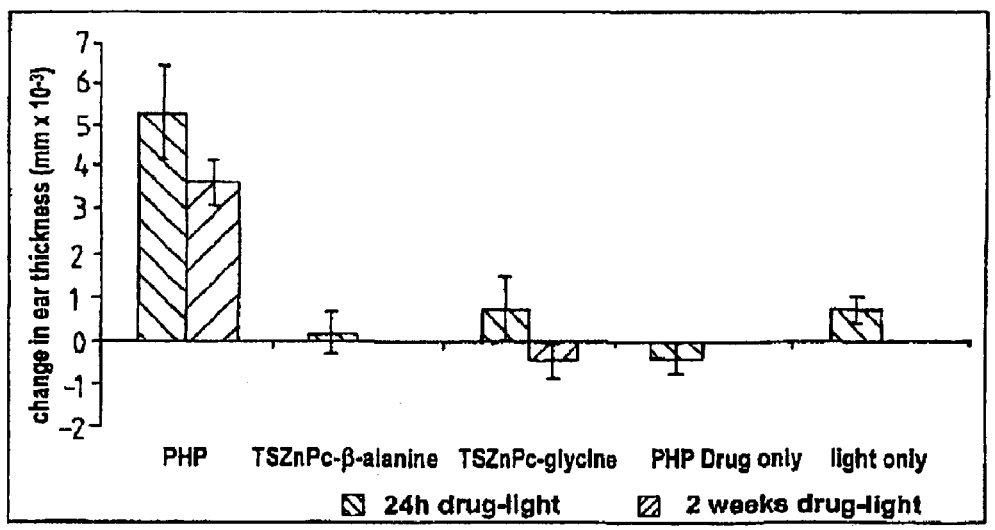
FIG. 7 depicts the ear-swelling response experienced by wistar rats at 24-hour post-illumination using various test compounds. The bars represent the mean of 4 mice±standard error.

CBA/Gy mice were injected with sensitiser at 16.7 µmol/kg. At 24 h post drug injection ears were exposed to broad band white light from a xenon arc lamp (25 J/cm$^2$, 30 mW/cm$^2$). Change in ear thickness was measured as: ear thickness at 24 h post illumination minus ear thickness pre-illumination. Light exposure and ear measurements were repeated at 2 weeks post drug injection on the previously untreated ear. Results are shown in FIG. 7. Increased ear thickness measures increased skin photosensitivity.

(E) Skin Coloration

Certain photosensitiser drugs can cause a transient skin coloration immediately after drug administration. Whilst this may not present a physical health problem, it may cause psychological difficulties and make treatment cosmetically unacceptable. Compounds in the present invention have therefore been assessed for skin coloration against an acceptable limit. Data in both rat and mouse models are shown below.

(1) Skin Coloration—Wistar Rats

Figure 8:
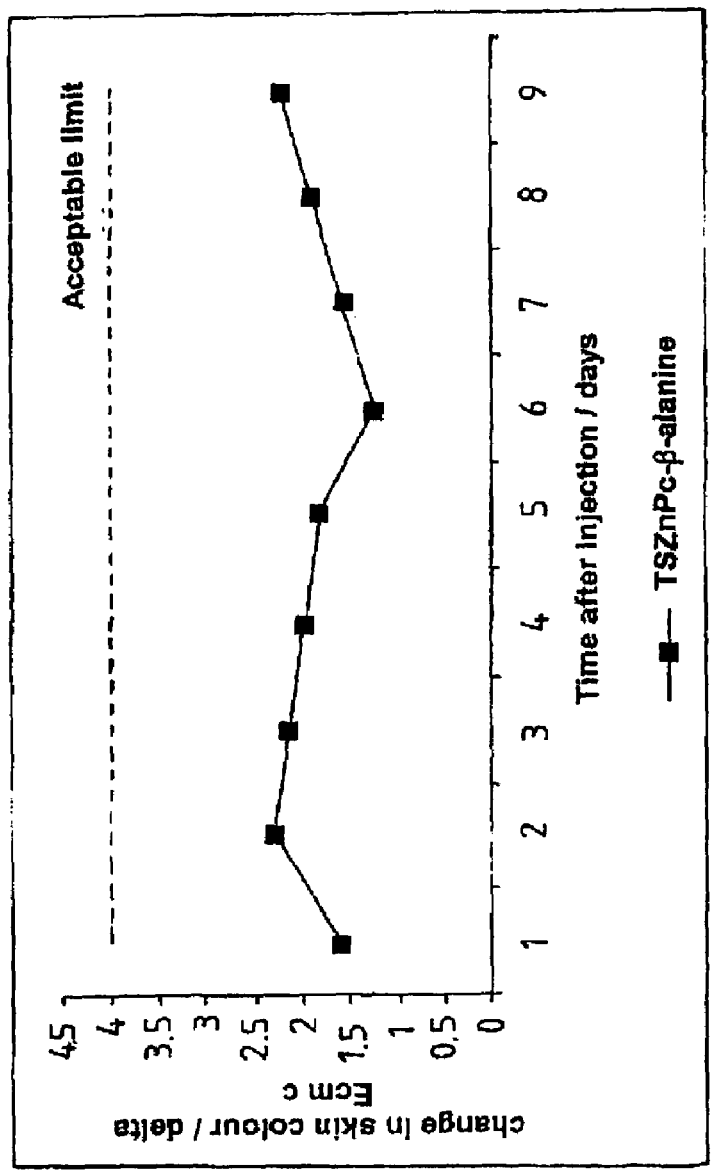
FIG. 8 depicts a measurement of the induced skin coloration in wistar rats following i.v. injection of TSZnPc-beta-alanine at 10 mg/kg.

The skin of Wistar rats ears was depilated and rats were injected with sensitiser at 0.5, 2, 5 or 10 mg/kg. Skin coloration was measured daily using a sphere spectrophotometer and compared to the skin of a control rat (no drug). Results are shown in FIG. 8 for 10 mg/kg.

(2) Skin Coloration—CBA/Gy Mice

Figure 9:
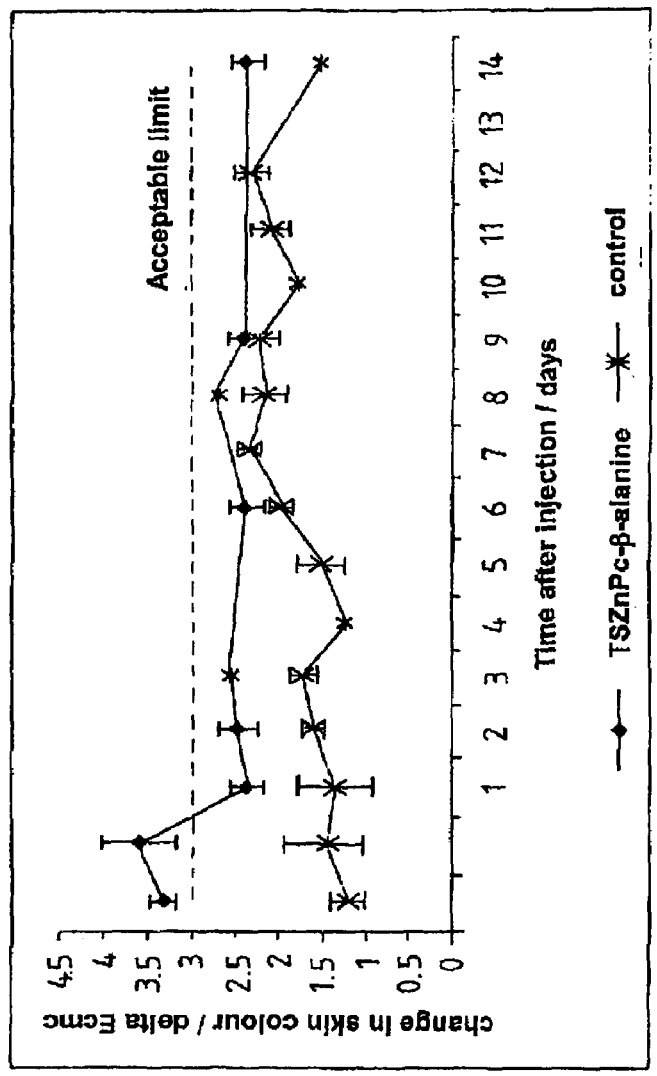
FIG. 9 depicts a comparison of the measured induced skin coloration in CBA/Gy mice following injection of TSZnPc-beta-alanine or a control at 16.7 μmol/kg at different intervals.

The skin of CBA/Gy mice was depilated and skin coloration was measured using a sphere spectrophotometer. Mice were injected with sensitiser at 16.7 16.7 µmol/kg. Skin colour was remeasured at 10 mins, 3 h, 24 h then daily for 14 days or until within control levels. Results are shown in FIG. 9.

The invention claimed is:

1. A compound comprising a photosensitising chromophoric system (Phot), a sulphonamido functionality and a carboxy functionality or a pharmaceutically acceptable salt thereof, in which the Phot is selected from a residue of a metal-free phthalocyanine, a metal phthalocyanine, a benzoporphyrin, a purpurin, a chlorin, a bacteriochlorin, a tetraarylporphyrin, a porphycene and a texaphyrin, wherein:

the metal phthalocyanine carries from 1 to 8 substituents selected from —SO$_2$NY—X—CO$_2$H and —Z—SO$_2$NY—X—CO$_2$H, and the chlorin, bacteriochlorin and tetraarylporphyrin carry from 1 to 4 substituents selected from —SO$_2$NY—X—CO$_2$H and —Z—SO$_2$NY—X—CO$_2$H, in which
- X is a linear or branched alkyl or alkenyl group having from 0 to 5 carbon atoms which arts optionally substituted by at least one of hydroxyl, methoxy, ethoxy, fluoro, chloro, carboxymethyl or carboxyamide;
- Y is hydrogen or a an linear or branched alkyl having from 1 to 5 carbon atoms which are optionally substituted by at least one hydroxy; and
- Z is a linking group;

excluding the compounds tetrasulphonylaminoglycine zinc (II) phthalocyanine, tetrasulphonylamino β-alanine zinc (II) phthalocyanine, tetrasulphonylamino-α-alanine zinc (II) phthalocyanine, tetrasulphonylamino butyric acid zinc (II) phthalocyanine, tetrasulphonylamino valeric acid zinc (II) phthalocyanine, and tetrasulphonylamino caproic acid zinc (II) phthalocyanine.

2. A pharmaceutical composition comprising one or more compounds comprising a photosensitising chromophoric system (Phot), a sulphonamido functionality and a carboxy functionality, in which the Phot is selected from a residue of a metal-free phthalocyanine, a metal phthalocyanine, a benzoporphyrin, a purpurin, a chlorin, a bacteriochlorin, a tetraarylporphyrin, a porphycene and a texaphyrin, wherein:

the chlorin, bacteriochlorin and tetraarylporphyrin carry from 1 to 4 substituents selected from —SO$_2$NY—X—CO$_2$H and —Z—SO$_2$NY—X—CO$_2$H, in which
- X is a linear or branched alkyl or alkenyl group having from 0 to 5 carbon atoms which are optionally substituted by at least one of hydroxyl, methoxy, ethoxy, fluoro, chloro, carboxymethyl or carboxyamide;
- Y is hydrogen or a linear or branched alkyl having from 1 to 5 carbon atoms which are optionally substituted by at least one hydroxy; and
- Z is a linking group, together with one or more pharmaceutically acceptable diluents, excipients or adjuvants.

3. A method of photodynamic therapy (PDT) comprising
- administering a photosensitiser to target tissue, and
- activating the photosensitiser by exposure to light, wherein the photosensitiser comprises a compound having a photosensitising chromophoric system (Phot), a sulphonamido functionality and a carboxy functionality, in which the Phot is selected from a residue of a metal-free phthalocyanine, a metal phthalocyanine, a benzoporphyrin, a purpurin, a chlorin, a bacteriochlorin, a tetraarylporphyrin, a porphycene and a texaphyrin, wherein:

the metal phthalocyanine carries from 1 to 8 substituents selected from —SO$_2$NY—X —CO$_2$H and —Z—SO$_2$NY—X—CO$_2$H, and the chlorin, bacteriochlorin and tetraarylporphyrin carry from 1 to 4 substituents selected from —SO$_2$NY—X—CO$_2$H and —Z—SO$_2$NY—X—CO$_2$H, in which
- X is a linear or branched alkyl or alkenyl group having from 0 to 5 carbon atoms which are optionally substituted by at least one of hydroxyl, methoxy, ethoxy, fluoro, chloro, carboxymethyl or carboxyamide;
- Y is hydrogen or a linear or branched alkyl having from 1 to 5 carbon atoms which are optionally substituted by at least one hydroxy; and
- Z is a linking group.

4. A method of photochemical internalisation to assist with the uptake of a drug or other biologically active molecule into a cell or a sub-cellular compartment within a cell, the method comprising administering a photosensitisor and the drug or other biologically active molecule to the cell in any order, and thereafter activating the photosensitiser in the presence of the drug or other biologically active molecule, wherein the photosensitiser comprises a compound having a photosensitising chromophoric system (Phot), a sulphonamido functionality and a carboxy functionality, in which the Phot is selected from a residue of a metal-free phthalocyanine, a metal phthalocyanine, a benzoporphyrin, a purpurin, a chlorin, a bacteriochlorin, a tetraarylporphyrin, a porphycene bacteriochlorin, a tetraarylporphyrin, a porphycene and a texaphyrin, wherein:

the metal phthalocyanine carries from 1 to 8 substituents selected from —SO$_2$NY—X—CO$_2$H and —Z—SO$_2$NY—X—CO$_2$H, and the chlorin, bacteriochlorin and tetraarylporphyrin carry from 1 to 4 substituents selected from —SO$_2$NY—X—CO$_2$H and —Z—SO$_2$NY—X—CO$_2$H, in which
- X is a linear or branched alkyl or alkenyl group having from 0 to 5 carbon atoms which are optionally substituted by at least one of hydroxyl, methoxy, ethoxy, fluoro, chloro, carboxymethyl or carboxyamide;
- Y is hydrogen or a linear or branched alkyl having from 1 to 5 carbon atoms which are optionally substituted by at least one hydroxy; and
- Z is a linking group.

5. The method of claim 3 or claim 4 wherein the sulphonamido functionality and carboxy functionality of said compound are linked directly or via an optionally substituted, saturated or unsaturated, linear or branched hydrocarbon group.

6. The method of claim 3 or claim 4 wherein said compound is of formula (I):

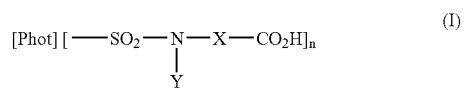

or a salt thereof, wherein:

Phot, X and Y are as defined in claim 3, and n is an integer of from 1 to 8.

7. The method of claim 3 or claim 4 wherein the sulphur atom (S) of the sulphonamido functionality of said compound is linked directly to the Phot or is linked via a linker group —Z— to the Phot.

8. The method of claim 3 or claim 4 wherein the Phot of said compound is of formula (B):

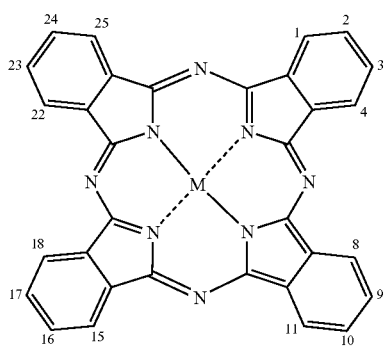 (B)

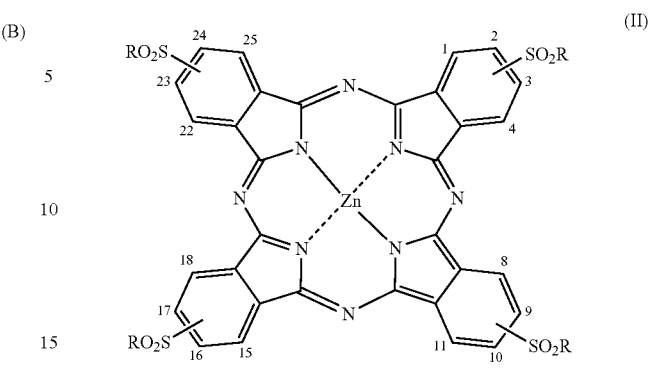 (II)

which carries from 1 to 8 substituents of formula —SO$_2$NY—X—CO$_2$H or of formula —Z—SO$_2$NY—X—CO$_2$H in which X, Y and Z are as defined in claim 3 and in which M is a central atom or group selected from H, Zn, ClAl, HOAl, (Ca, Mg, Sn, ClGa, ClIn, HOIn, Cl$_2$Si, (R$^1$O)$_2$Si and R$_2$O—(CH$_2$CH$_2$O)$_p$CH$_2$CH$_2$—, wherein R$^1$ is H, linear or branched C$_{1-10}$ alkyl, R$^2$ is H, CH$_1$ or C$_2$H$_5$, p is an integer from 1 to 4, and when M is H, two H's are present.

9. The method of claim 3 or claim 4 wherein when the Phot is a metal phthalocyanine, the compound is of formula (II):

wherein each R independently is —NY—X—CO$_2$H, and X and Y are as defined in claim 3.

10. The method of claim 9 wherein each R is —NY—X—CO$_2$H;

X is selected from —CH$_2$—, —CH$_2$CH$_2$—, —CH(CH$_3$)—, —(CH$_2$)$_3$, —(CH$_2$)$_4$— and —(CH$_2$)$_3$; and Y is H.

11. The method of claim 3 wherein said PDT is used in the treatment is of pre-cancerous conditions, cancer of the skin, lungs, brain, eye, colon, bladder, cervix and oesophagus, ophthalmological disease, cardiovascular disease, arteriosclerosis, and restenosis, autoimmune diseases, skin diseases, endometriosis and mennorrhagia.

12. The method of claim 3 wherein said PDT provides an anti-microbial effect.

* * * * *